(12) United States Patent
Eddy et al.

(10) Patent No.: US 12,383,464 B2
(45) Date of Patent: *Aug. 12, 2025

(54) INTRAVENOUS FLUID BAG WITH AN INTEGRATED VALVE HAVING A SEAL WITH A COMPRESSED STATE THAT PERMITS FLUID FLOW INTO THE BAG AND A RELAXED STATE PREVENTING FLUID FLOW

(71) Applicant: Parasol Medical LLC, Buffalo Grove, IL (US)

(72) Inventors: Patrick E. Eddy, Allendale, MI (US); Michael D. Kilcran, Antioch, IL (US)

(73) Assignee: Parasol Medical, LLC, Buffalo Grove, IL (US)

( * ) Notice: Subject to any disclaimer, the term of this patent is extended or adjusted under 35 U.S.C. 154(b) by 1031 days.

This patent is subject to a terminal disclaimer.

(21) Appl. No.: 17/404,661

(22) Filed: Aug. 17, 2021

(65) Prior Publication Data
US 2021/0369564 A1 Dec. 2, 2021

Related U.S. Application Data

(63) Continuation of application No. 15/938,953, filed on Mar. 28, 2018, now Pat. No. 11,129,771.

(51) Int. Cl.
| | |
|---|---|
| A61J 1/14 | (2023.01) |
| A61J 1/10 | (2006.01) |
| A61J 1/20 | (2006.01) |
| A61M 39/04 | (2006.01) |
| A61M 39/24 | (2006.01) |
| A61M 39/26 | (2006.01) |

(52) U.S. Cl.
CPC ............... *A61J 1/1475* (2013.01); *A61J 1/10* (2013.01); *A61J 1/14* (2013.01); *A61J 1/201* (2015.05);
(Continued)

(58) Field of Classification Search
CPC .... A61J 1/10; A61J 1/14; A61J 1/1406; A61J 1/1412; A61J 1/1431; A61J 1/1468;
(Continued)

(56) References Cited

U.S. PATENT DOCUMENTS

4,412,573 A * 11/1983 Zdeb ........................ B23P 11/02
604/408
5,088,994 A * 2/1992 Porat ........................ B29C 66/71
604/408
(Continued)

*Primary Examiner* — Philip R Wiest
(74) *Attorney, Agent, or Firm* — Price Heneveld LLP (57) ABSTRACT

An intravenous fluid bag comprising: a primary chamber configured to retain a liquid; a valve in fluid communication with the primary chamber, the valve including a housing, a spike element, and a seal, with the housing surrounding the seal, which surrounds the spike element; the spike element having a first end culminating in a tip, a second end having an inner conduit, and one or more through holes between the tip and the second end in fluid communication with the inner conduit forming part of a continuous liquid passageway in fluid communication with the primary chamber; the seal having a relaxed state preventing fluid flow through the valve, and the seal having a compressed state through which the through holes of the spike element extend allowing fluid flow from a source external the intravenous fluid bag, through the through holes, through the inner conduit, and into the primary chamber.

15 Claims, 8 Drawing Sheets

(52) U.S. Cl.
CPC ............ *A61M 39/04* (2013.01); *A61M 39/24* (2013.01); *A61L 2300/208* (2013.01); *A61L 2300/404* (2013.01); *A61M 39/26* (2013.01)

(58) Field of Classification Search
CPC ...... A61J 1/1475; A61J 1/1481; A61J 1/1487; A61J 1/2093; A61M 39/04; A61M 39/24; A61M 39/26
See application file for complete search history.

(56) References Cited

U.S. PATENT DOCUMENTS

| | | | |
|---|---|---|---|
| 5,685,866 | A | 11/1997 | Lopez |
| 8,323,259 | B2 | 12/2012 | Smith et al. |
| 8,323,269 | B2 * | 12/2012 | Shachar .............. A61M 5/1723 604/891.1 |
| 9,433,708 | B2 | 9/2016 | Eddy |
| 11,129,771 | B2 * | 9/2021 | Eddy ..................... A61J 1/1481 |
| 2004/0241041 | A1 * | 12/2004 | Woodworth .............. A61L 2/00 250/455.11 |
| 2010/0126894 | A1 * | 5/2010 | Koukol .............. B65D 55/0854 206/459.1 |
| 2011/0282302 | A1 * | 11/2011 | Lopez .................. A61M 39/26 604/246 |
| 2015/0352320 | A1 | 12/2015 | Eddy |

* cited by examiner

INTRAVENOUS FLUID BAG WITH AN INTEGRATED VALVE HAVING A SEAL WITH A COMPRESSED STATE THAT PERMITS FLUID FLOW INTO THE BAG AND A RELAXED STATE PREVENTING FLUID FLOW

CROSS-REFERENCE TO RELATED APPLICATIONS

This Application is a continuation of application Ser. No. 15/938,953 filed on 28 Mar. 2018 (now U.S. Pat. No. 11,129,771), the entirety of which is incorporated herein by reference in its entirety.

FIELD OF THE DISCLOSURE

The present disclosure generally relates to an intravenous fluid bag.

BACKGROUND OF THE DISCLOSURE

An intravenous fluid bag sometimes includes an injection port. The injection port allows for another fluid, which can contain a medicament, to be injected into the intravenous fluid bag. The injection port sometimes requires a metal needle to pierce the injection port to inject the medicament-containing fluid into the intravenous fluid bag. The use of metal needles can cause injury, can damage the intravenous fluid bag, and can require special disposal processes.

BRIEF SUMMARY OF THE DISCLOSURE

According to a first aspect of the present disclosure, an intravenous fluid bag includes a primary chamber configured to retain a liquid. A valve is in fluid communication with the primary chamber. The valve includes a housing, a spike element, and a seal, with the housing surrounding the seal, which surrounds the spike element. The spike element includes a first end culminating in a tip, a second end having an inner conduit, and one or more through holes between the tip and the second end in fluid communication with the inner conduit forming part of a continuous liquid passageway in fluid communication with the primary chamber. The second end is disposed closer to the primary chamber than the tip. The seal includes a first end, a second end, and a seal cap at the first end. The seal includes a relaxed state in which the seal forms a liquid tight seal over the through holes preventing fluid flow through the valve. The seal includes a compressed state through which the tip and the through holes of the spike element extend allowing fluid flow from a source external the intravenous fluid bag, through the through holes, through the inner conduit, and into the primary chamber.

Embodiments of the first aspect of the invention can include any one or a combination of the following features:
  a plastic sleeve surrounds a length of the housing of the valve and holds the valve in place;
  the primary chamber is formed of plastic that is contiguous with the plastic sleeve that surrounds the housing of the valve;
  a plastic sleeve surrounds the inner conduit of the spike element of the valve and holds the valve in place;
  the primary chamber is formed of plastic that is contiguous with the plastic sleeve that surrounds the inner conduit of the spike element of the valve;
  the inner conduit has an outer surface that is cylindrical;
  the housing includes a hollow interior that surrounds the tip of the spike element;
  the inner conduit of the spike element is not in fluid communication with the hollow interior of the housing when the seal is in the relaxed state;
  the housing has an outer surface and threads extending from the outer surface configured to couple with a syringe;
  the one or more through holes are 18 gauge in size or larger;
  the first end of the seal has a flat external surface not covered by the housing;
  the housing has a first end that is open forming an opening;
  the first end of the housing at the opening and the flat external surface of the seal are flush;
  the seal forms a conically shaped cavity in which the tip of the spike element is disposed when the seal is in the relaxed state;
  the seal includes a plurality of ringed wall portions that collapse when the seal moves from the relaxed state to the compressed state;
  the seal cap includes a piercing through which the tip and the through holes of the spike element extend when the seal is in the compressed state;
  when the seal is in the relaxed state, the piercing is closed and does not permit the flow of fluid through the seal cap; and
  an antimicrobial coating including a silane quaternary ammonium ion or salt thereof.

According to a second aspect of the present disclosure, a method of introducing a second liquid into an intravenous fluid bag that contains a first liquid includes presenting an intravenous fluid bag. A primary chamber retains at least the first liquid. A valve is in fluid communication with the primary chamber. The valve includes a housing, a spike element, and a seal, with the housing surrounding the seal, which surrounds the spike element. The spike element includes a first end culminating in a tip, a second end having an inner conduit, and one or more through holes between the tip and the second end in fluid communication with the inner conduit forming part of a continuous liquid passageway in fluid communication with the primary chamber. The second end is disposed closer to the primary chamber than the tip. The seal includes a first end, a second end, and a seal cap at the first end. The seal includes a relaxed state in which the seal forms a liquid tight seal over the through holes preventing fluid flow through the valve. The seal has a compressed state through which the tip and the through holes of the spike element extend when the seal is in the compressed state allowing fluid flow from a source external the intravenous fluid bag, through the through holes, through the inner conduit, and into the primary chamber. A second liquid container includes a second liquid. A valve interaction portion includes a seal compression element surrounding a liquid outlet. The second liquid container includes a pressure inducing element. The seal of the valve of the intravenous fluid bag is compressed from the relaxed state into the compressed state with the seal compression element of the second liquid container. The second liquid is caused to flow from the second liquid container through the valve of the intravenous fluid bag and into the primary chamber of the intravenous fluid bag with the first liquid.

Embodiments of the second aspect of the invention can include any one or a combination of the following features:
  the valve interaction portion of the second liquid container further comprising a thread receiver;

the housing of the valve of the intravenous fluid bag has an outer surface and threads extending from the outer surface;

compressing the seal of the valve of the intravenous fluid bag into the compressed state occurs while the thread receiver is receiving the threads of the housing of the valve of the intravenous fluid bag;

the one or more through holes are 18 gauge in size or larger;

the liquid outlet of the valve interaction portion of the second liquid container is 18 gauge in size or larger;

the seal of the intravenous fluid bag including a plurality of ringed wall portions;

compressing the seal of the valve of the intravenous fluid bag into the compressed state causes the plurality of ringed wall portions to collapse;

moving the seal compression element away from the second end of the seal, thereby allowing the seal of the valve of the intravenous fluid bag to move to the relaxed state;

the intravenous fluid bag further comprising an outlet port; and the method further comprising: causing the first liquid and the second liquid in the primary chamber of the intravenous fluid bag to exit the intravenous fluid bag through the outlet port.

These and other features, advantages, and objects of the present disclosure will be further understood and appreciated by those skilled in the art by reference to the following specification, claims, and appended drawings.

DETAILED DESCRIPTION

For purposes of description herein, it is to be understood that the specific devices and processes illustrated in the attached drawings, and described in the following specification are simply exemplary embodiments of the inventive concepts defined in the appended claims. Hence, physical characteristics relating to the embodiments disclosed herein are not to be considered as limiting, unless the claims expressly state otherwise.

Figure 1:
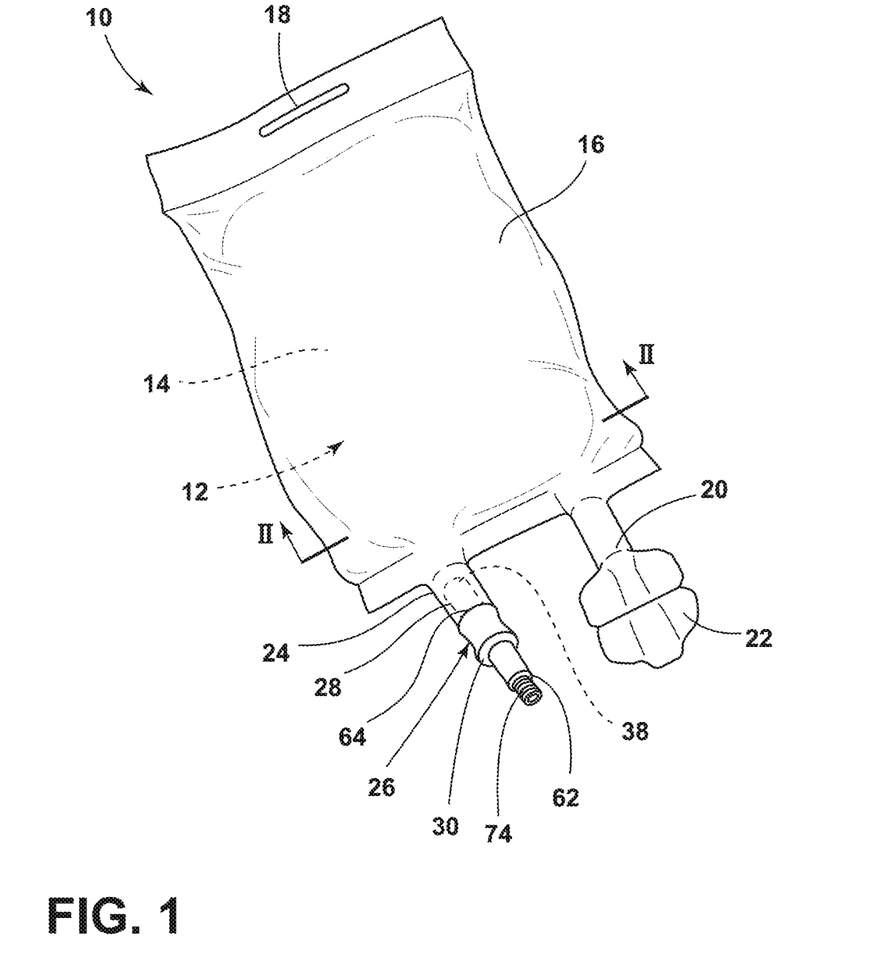
FIG. 1 is a perspective view of an embodiment of an intravenous fluid bag, illustrating an inlet port and a valve in communication with the inlet port.
Figure 2:
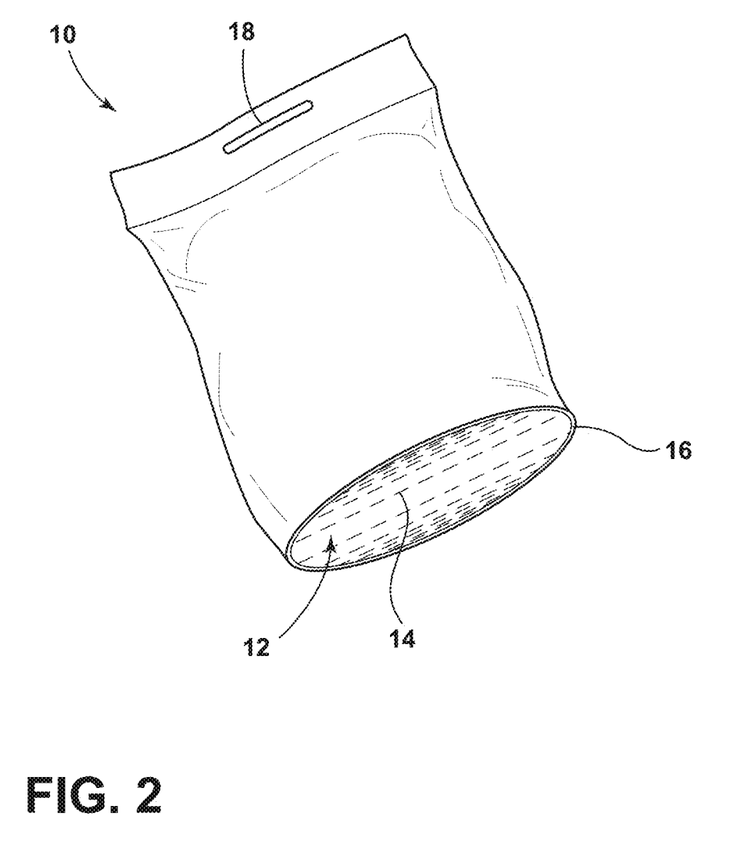
FIG. 2 is a perspective view of the intravenous fluid bag of FIG. 1, taken along cross-section II-II of FIG. 1, illustrating a liquid within a primary chamber of the intravenous fluid bag.

Referring now to FIGS. 1-2, an intravenous fluid bag 10 includes a primary chamber 12 to retain a liquid 14. A plastic material 16 forms the primary chamber 12, but other materials may be suitable. The plastic material 16 is transparent to allow the contents (e.g., the liquid 14) of the primary chamber 12 to be seen. The plastic material 16 need not be transparent however. The intravenous fluid bag 10 includes an aperture 18, which allows the intravenous fluid bag 10 to be hung on a pole (not illustrated) during use. The intravenous fluid bag 10 further includes an outlet port 20, which is covered by a removable cap 22. The removable cap 22 can be removed, allowing a spike (not illustrated) to be inserted into the outlet port 20 so that the liquid 14 (any additional liquid added to the primary chamber 12, as discussed below) of the intravenous fluid bag 10 can be administered to the patient (also not illustrated).

The intravenous fluid bag 10 further includes an inlet port 24. The inlet port 24 includes a valve 26, which operates to selectively permit or deny fluid communication through the inlet port 24 into the primary chamber 12. The valve 26 is in fluid communication with the primary chamber 12. A plastic sleeve 28 (e.g., a tubular portion) surrounds a portion of the valve 26 to hold the valve 26 in place as a component of the intravenous fluid bag 10. The plastic sleeve 28 is contiguous with the plastic material 16 that forms the primary chamber 12.

Referring now additionally to FIGS. 3-6, the valve 26 includes a housing 30, a spike element 32, and a seal 34. The seal 34 surrounds a portion of the spike element 32. The housing 30 surrounds the seal 34. The housing 30 encloses a portion of the seal 34 and the spike element 32 to function as the valve 26 in the manner set forth in U.S. Pat. Nos. 5,685,866 and 9,433,708, which are both incorporated herein by reference in their entireties.

Figure 5:
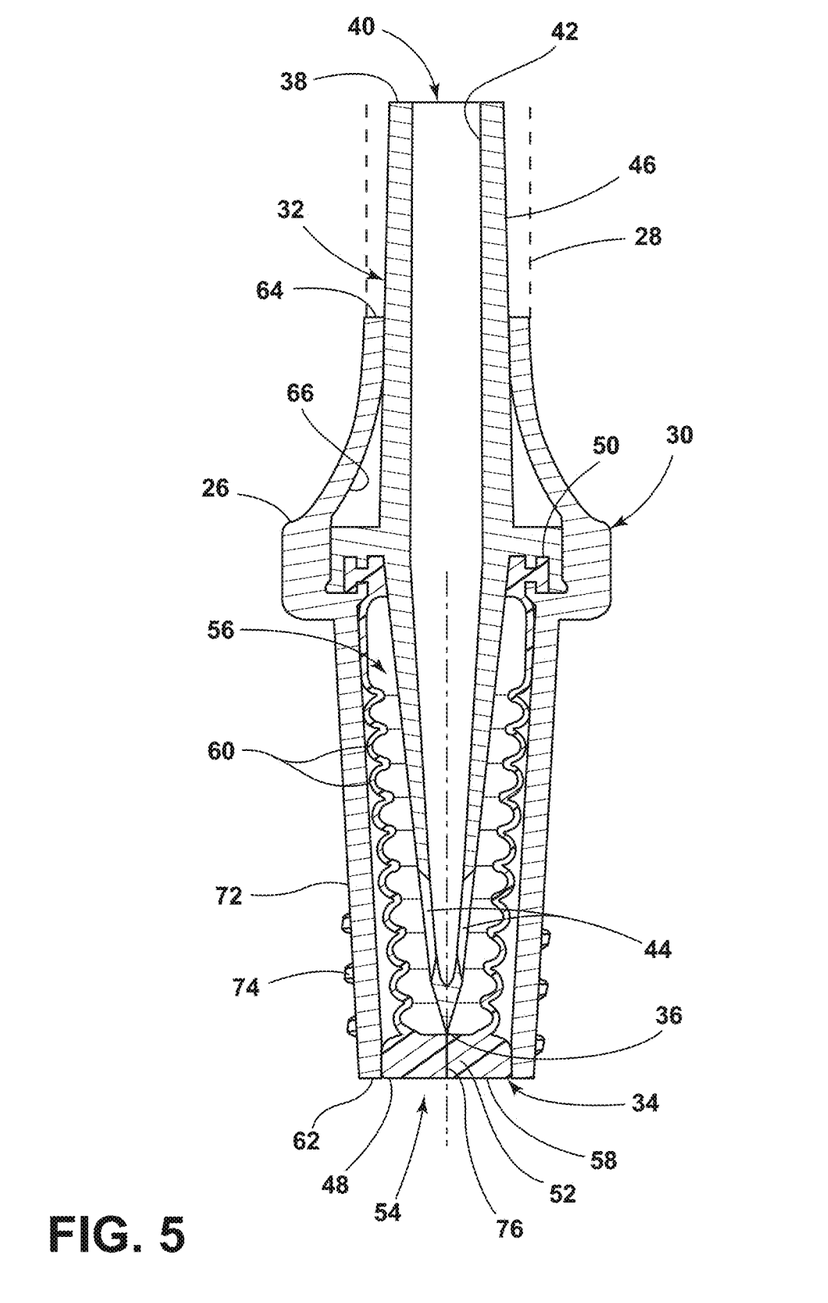
FIG. 5 is a front view of a vertical cross-section of the valve of the intravenous fluid bag of FIG. 1, illustrating the housing securing the valve and the spike element, and the spike element having an inner conduit in fluid communication with the primary chamber of the intravenous fluid bag and in fluid communication with through holes near the tip of the spike element, and the seal in a relaxed state blocking further fluid communication beyond the valve.

The spike element 32 has a tip 36 defining a first end and a second end 38 with an opening 40 into an inner conduit 42. The spike element 32 has one or more through holes 44, which are in fluid communication with the inner conduit 42. The one or more through holes 44 are disposed between the tip 36 and the second end 38, and can be disposed adjacent the tip 36 as illustrated in FIG. 5. Because the one or more through holes 44 are in fluid communication with the inner conduit 42, the one or more through holes 44 are part of a continuous liquid passageway, via the inner conduit 42 and the opening 40, to the primary chamber 12 of the intravenous fluid bag 10. The one or more through holes 44 can be any size, but can be 18 gauge in size or larger to allow adequate fluid flow from an external liquid container, such as a syringe (discussed further below). The second end 38 of the spike element 32 is disposed closer to the primary chamber 12 than the tip 36. The spike element 32 has an outer surface 46 proximate the second end 38, which the outer surface 46 can be cylindrical as in the illustrated embodiment, but could be any desired shape.

Figure 6:
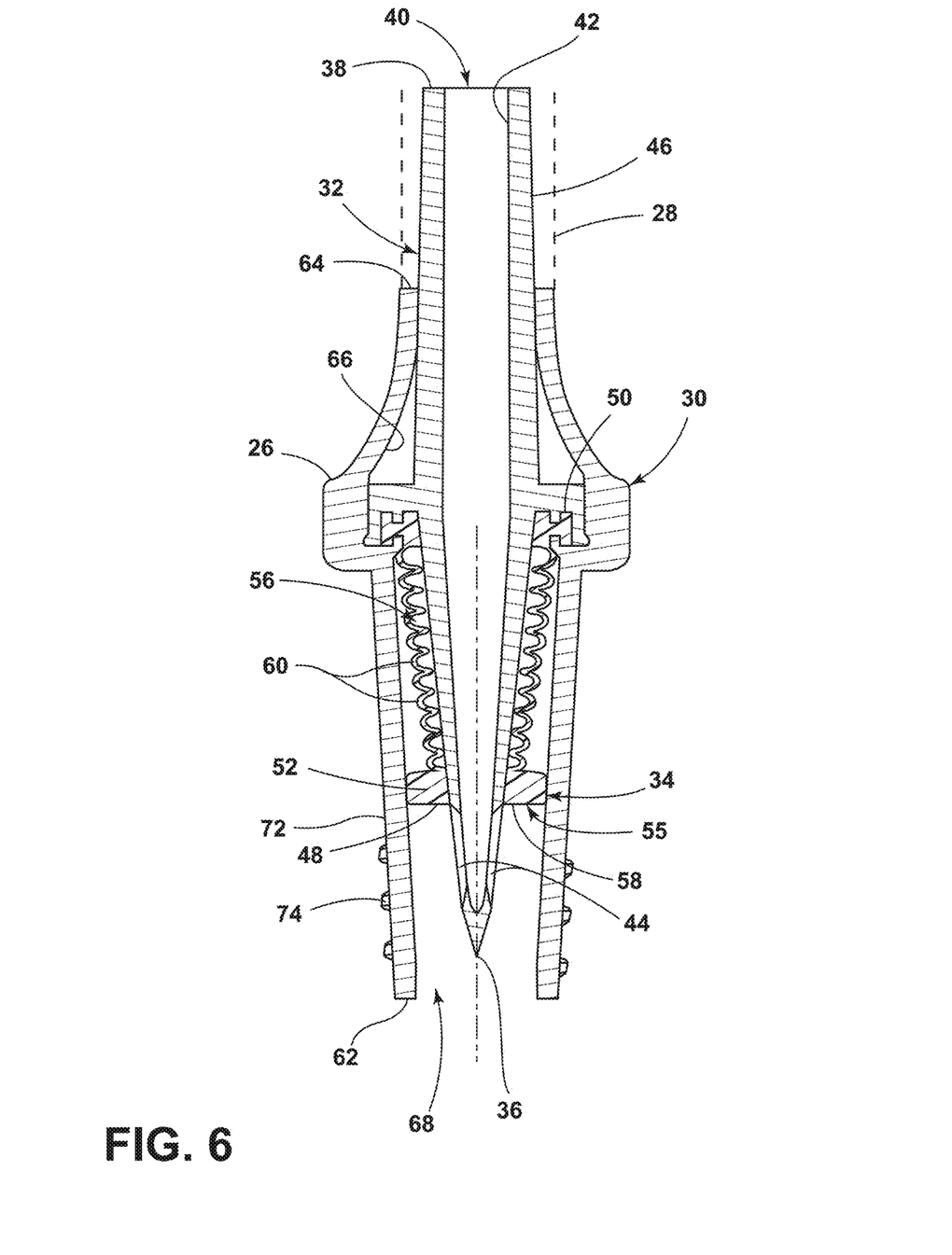
FIG. 6 is similar to FIG. 5 but illustrates the seal in a compressed state allowing fluid flow from a source beyond the valve, through the through holes of the spike element, through the inner conduit thereof, and into the primary chamber of the intravenous fluid bag.

The seal 34 has a first end 48 and a second end 50. The seal 34 has a seal cap 52 disposed at the first end 48. The seal 34 naturally maintains a relaxed state 54 (FIG. 5), but can be forced into a compressed state 55 (FIG. 6). In the relaxed state 54 (FIG. 5), the seal 34 forms a liquid tight seal over the one or more through holes 44 preventing fluid flow through the valve 26, such as from the primary chamber 12 of the intravenous fluid bag 10 through the spike element 32 and beyond the valve 26, or fluid flow in the opposite direction. The seal 34 has a generally hollow interior that forms a cavity 56. A portion of the spike element 32 is disposed in the cavity 56 in the seal 34. When the seal 34 is in the relaxed state 54, the tip 36 of the spike element 32 is disposed in the cavity 56. The cavity 56 can take a variety of shapes, such as the conical shape in the illustrated embodiment. The first end 48 of the seal 34 has an external surface 58, which in the illustrated embodiment, is generally flat (planar). The seal 34 of the illustrated embodiment includes a plurality of ringed wall portions 60. When the seal 34 is forced from the relaxed state 54 to the compressed state 55, the plurality of ringed wall portions 60 collapse upon each other. The plurality of ringed wall portions 60 can function as a spring element that assists the seal 34 in returning to the relaxed state 54 from the compressed state 55 when the force upon the seal 34 is removed.

The housing 30 has a first end 62, a second end 64, and a hollow interior 66, within which the spike element 32 and the seal 34 are secured. The hollow interior 66 surrounds the tip 36 of the spike element 32 and, in the illustrated embodiment, the seal cap 52 of the seal 34. Both the first end 62 and the second end 64 of the housing 30 are open forming openings 68, 70, respectively. The first end 62 of the housing 30 surrounds the seal cap 52 of the seal 34 at the opening 68 such that the first end 62 of the housing 30 at the opening 68 and the external surface 58 of the seal 34 are flush. When the seal 34 is in the relaxed state 54 (FIG. 5), the inner conduit 42 of the spike element 32 is not in fluid communication with the hollow interior 66 of the housing 30. In the relaxed state 54, the seal 34 prevents fluid in the inner conduit 42 of the spike element 32 from flowing into the hollow interior 66 of the housing 30. The housing 30 has an outer surface 72 that extends between the first end 62 and the second end 64. The outer surface 72 can include threads 74 extending therefrom adjacent to the first end 62. The threads 74 permit a device with matching thread receivers, such as a syringe (discussed further below), to be coupled to the valve 26 via the housing 30.

In the compressed state 55 (FIG. 6), the tip 36 and the one or more through holes 44 of the spike element 32 extend through the seal cap 52. The seal cap 52 can include a piercing 76 through the seal cap 52 from the external surface 58 through to the cavity 56. The tip 36, and the one or more through holes 44 of the spike element 32, extend through the piercing 76 when the seal 34 transitions from the relaxed state 54 to the compressed state 55. When the seal 34 is in the compressed state 55, fluid can flow from a source external to the intravenous fluid bag 10, through the one or more through holes 44 of the spike element 32, through the inner conduit 42, and into the primary chamber 12 of the intravenous fluid bag 10 to mix with the liquid 14 already in the primary chamber 12. When the seal 34 is returned to the relaxed state 54, the piercing 76 through the seal cap 52 closes and does not permit the flow of fluid through the seal cap 52.

Figure 3:
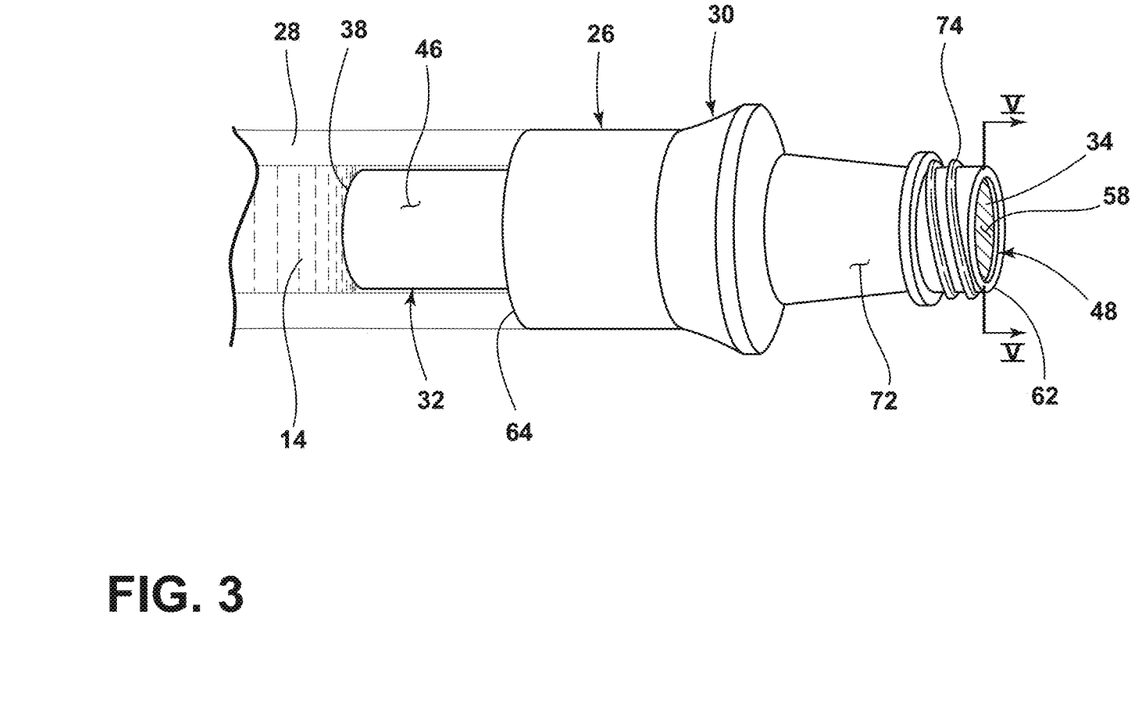
FIG. 3 is a perspective view of the valve of the intravenous fluid bag of FIG. 1, illustrating a plastic sleeve of the inlet port attached to the valve, surrounding an outer surface of a spike element of the valve.
Figure 4:
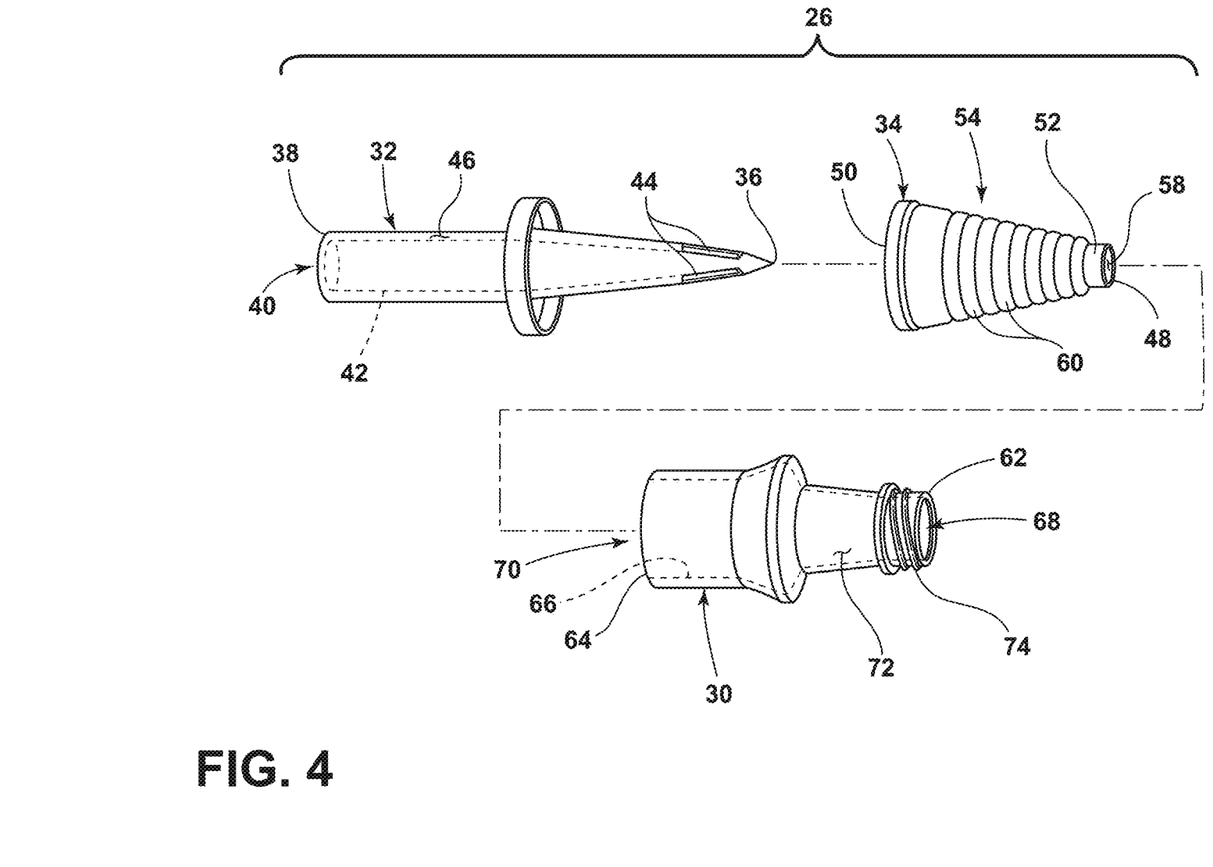
FIG. 4 is a blown up side view of the valve of the intravenous fluid bag of FIG. 1, illustrating a tip of the spike element being disposed in a seal of the valve, and the seal being disposed within a housing of the valve.

As mentioned above, the plastic sleeve 28 surrounds a portion of the valve 26 to hold the valve 26 in place to control fluid flow into and out of the primary chamber 12 of the intravenous fluid bag 10. For example, the plastic sleeve 28, as in the illustrated embodiment, can surround the outer surface 46 of the spike element 32. The plastic sleeve 28 can be heat shrunk over the outer surface 46. As another possible alternative, the plastic sleeve 28 can surround a portion of the housing 30 of the valve 26, such as the second end 64 of the housing 30. Regardless, the plastic sleeve 28 can thus hold the valve 26 in place and form a liquid tight seal around the valve 26.

Figure 7:
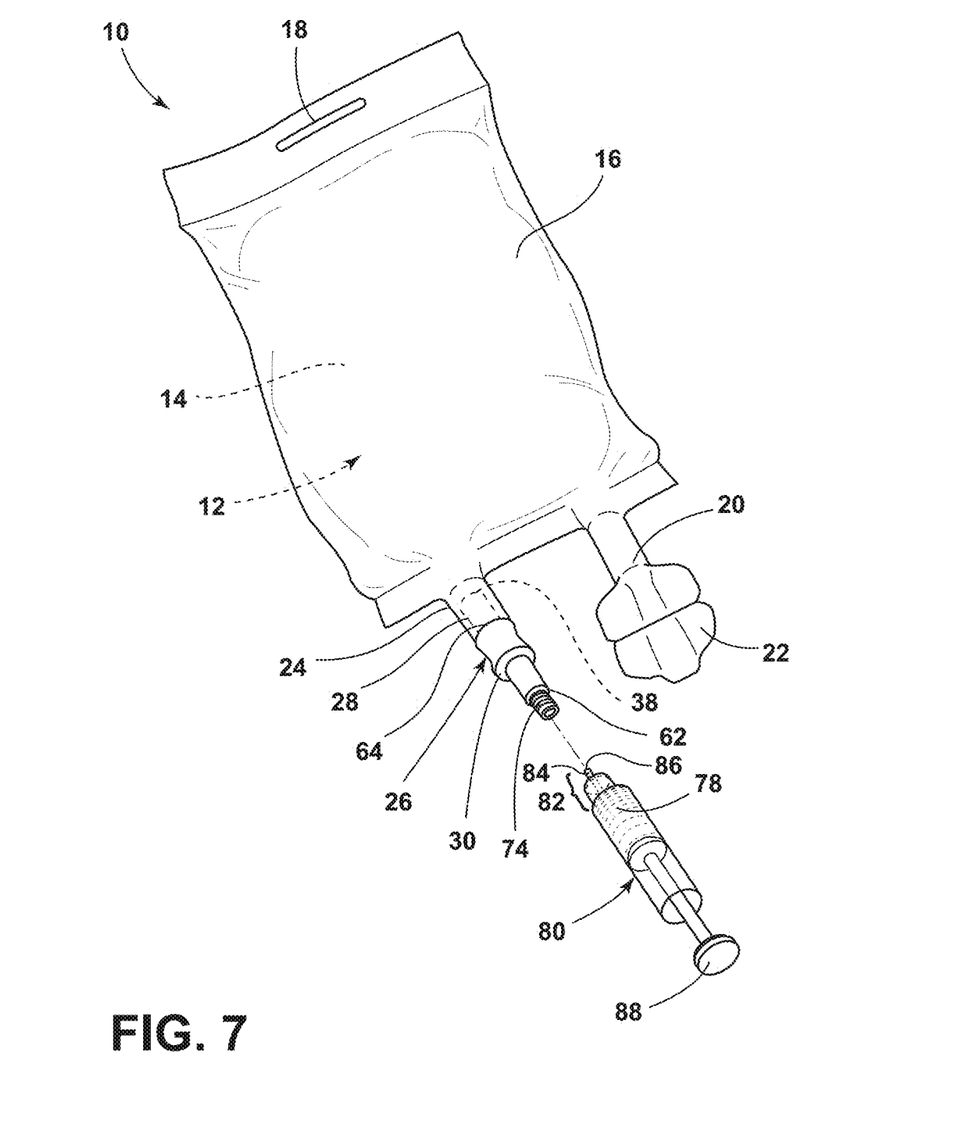
FIG. 7 is a perspective view of a second liquid container with a seal compression element being inserted into the first end of the housing of the valve of the intravenous fluid bag of FIG. 1 in order to cause a second liquid in the second liquid container to flow through the valve and into the primary chamber of the intravenous fluid bag with the liquid already in the primary chamber of the intravenous fluid bag.
Figure 8:
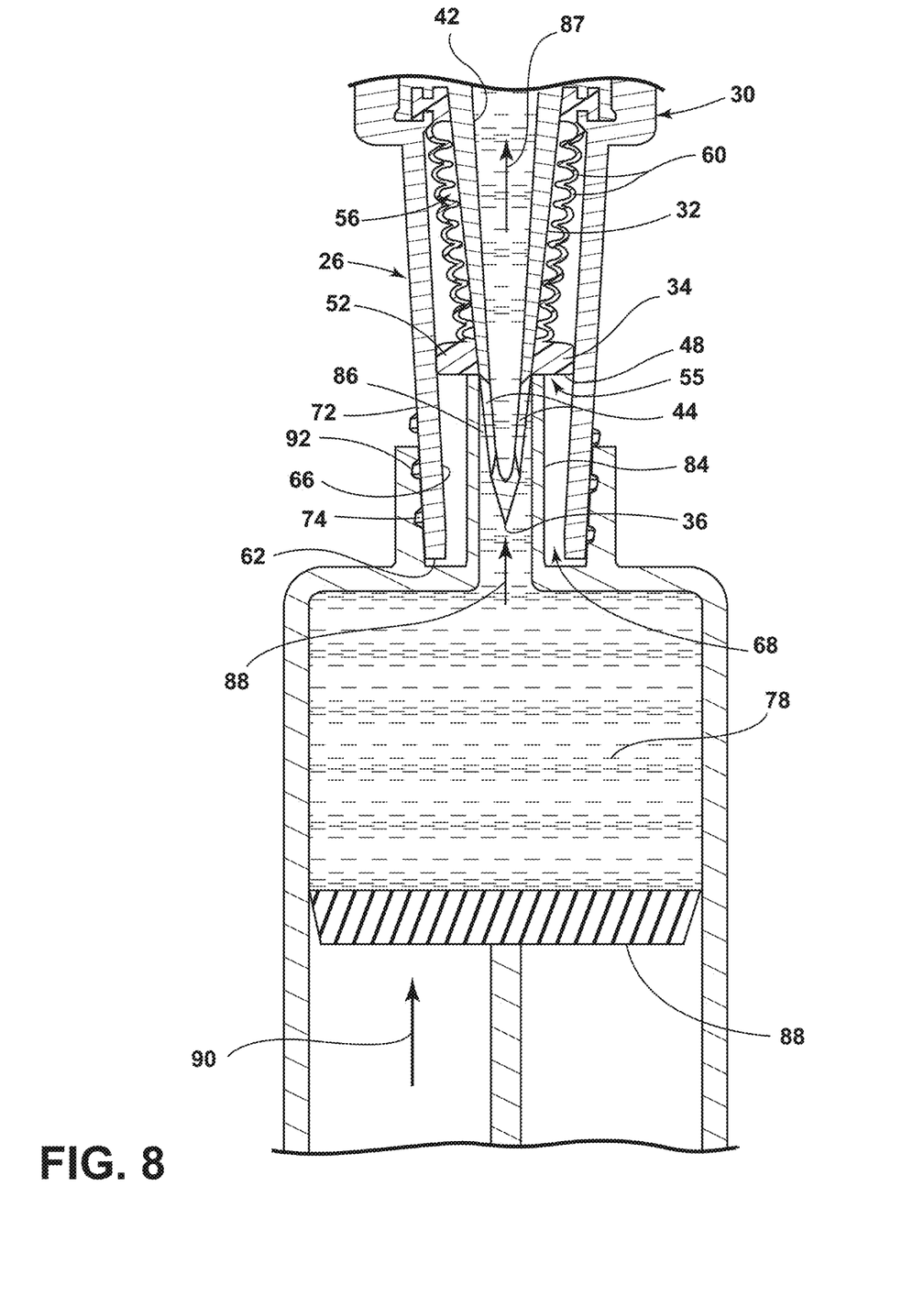
FIG. 8 is a front view of a vertical cross-section of the second liquid container coupled to the valve via a thread receiver receiving a thread of the housing, the top and through holes of the spike element within a liquid outlet of the second liquid container as the seal compression element forces the seal into the compressed state allowing a pressure inducing element of the second liquid container to force the second liquid out the liquid outlet, through the through holes and then the inner conduit of the spike element of the valve, and into the primary chamber of the intravenous fluid bag.

Referring now additionally to FIGS. 7-8, the intravenous fluid bag 10, including the valve 26, can be utilized to introduce a second liquid 78 into the intravenous fluid bag 10, which already contains the liquid 14. As discussed above, the intravenous fluid bag 10 includes a primary chamber 12 that retains the liquid 14. It may be desirable to add the second liquid 78, contained in a second liquid container 80, into the intravenous fluid bag 10 to mix with the liquid 14. The second liquid 78 can be medicine or otherwise have desirable properties such that it is desirable to add the second liquid 78 to the liquid 14 to administer intravenously the combined second liquid 78 and the liquid 14 to a patient (not illustrated). In addition to containing the second liquid 78, the second liquid container 80 includes a valve interaction portion 82. The valve interaction portion 82 includes a seal compression element 84 that surrounds a liquid outlet 86. The second liquid container 80 further includes a pressure inducing element 88.

The seal compression element 84 of the second liquid container 80 is inserted into the opening 68 of the first end 62 of the housing 30 of the valve 26 of the intravenous fluid bag 10, and pressed against the external surface 58 of the seal cap 52 of the seal 34. The seal compression element 84 then compresses the seal 34 from the relaxed state 54 into the compressed state 55. The tip 36 and the one or more through holes 44 of the spike element 32 are disposed within the liquid outlet 86 of the seal compression element 84. The liquid outlet 86, like the one or more through holes 44, can be 18 gauge size or larger, but can also be smaller.

The second liquid 78 is then caused to flow in a direction 87 from the second liquid container 80, through the valve 26 of the intravenous fluid bag 10, and into the primary chamber 12 of the intravenous fluid bag 10. The second liquid 78 thus combines (mixes or potentially reacts) with the liquid 14. The second liquid 78 can be so caused to flow in the direction 87 by imparting a force 90 on the pressure inducing element 88. The pressure inducing element 88 forces the second liquid 78 into the liquid outlet 86, through the one or more through holes 44 of the spike element 32, through the inner conduit 42, and into the primary chamber 12 of the intravenous fluid bag 10.

The valve interaction portion 82 of the second liquid container 80 can further comprise a thread receiver 92. The thread receiver 92 is configured to receive the threads 74 extending from the outer surface 72 of the housing 30 of the valve 26. Twisting the second liquid container 80 while the tip 36 of the spike element 32 of the valve 26 is disposed in the seal compression element 84 can cause the thread receiver 92 to receive the threads 74 of the housing 30. Continued twisting of the second liquid container 80 can cause the seal compression element 84 to compress the seal 34 of the valve 26 into the compressed state 55.

When the second liquid 78 has been caused to enter the primary chamber 12 of the intravenous fluid bag 10, the seal compression element 84 can be moved out of the opening 68 at the first end 62 of the housing 30 and away from the second end 50 of the seal 34. Moving the seal compression element 84 in this manner allows the seal 34 to move from the compressed state 55 back to the natural relaxed state 54. The combined liquid 14 with the second liquid 78 can then be administered intravenously to the patient by causing the liquid 14 and the second liquid 78 mixture (or reaction product, if the second liquid 78 and the liquid 14 react) in the primary chamber 12 of the intravenous fluid bag 10 to exit the intravenous fluid bag 10 through the outlet port 20.

Every and any component of the intravenous fluid bag 10 described herein, or any combination thereof, can be coated with an antimicrobial substance. The antimicrobial coating includes a silane quaternary ammonium ion or salt thereof. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. To impart the antimicrobial coating, the component or components of the intravenous fluid bag 10 can be coated with a solution including the silane quaternary ammonium ion or salt thereof, as described above. In addition to the silane quaternary ammonium ion or salt thereof, the solution can further include a solvent. A preferred solvent is isopropyl alcohol. The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution. As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 0.02 percent 3-(trimethoxysilyl)propyldimethyloctadecyl ammonium chloride, and 34.19 percent deionized water.

It is to be understood that variations and modifications can be made on the aforementioned structure without departing from the concepts of the present disclosure, and further it is to be understood that such concepts are intended to be covered by the following claims unless these claims by their language expressly state otherwise.

What is claimed is:

1. A method of manufacturing an intravenous fluid bag comprising:
   heat shrinking a plastic sleeve, which is contiguous with a plastic material forming a primary chamber configured to retain a liquid, over an outer surface of a valve;
   wherein, after the heat shrinking, the plastic sleeve holds the valve in place and forms a liquid tight seal around the valve and the valve is in fluid communication with the primary chamber.

2. The method of claim 1, wherein
   the valve comprises a housing, a seal that the housing surrounds, and a spike element that the seal surrounds; and
   the spike element comprises the outer surface over which the plastic sleeve is heat shrunk.

3. The method of claim 2, wherein
   the housing comprises (i) an outer surface, different than the outer surface of the valve over which the plastic sleeve is heat shrunk, and (ii) threads extending from the outer surface of the housing that are configured to couple with a syringe.

4. The method of claim 2, wherein
   the spike element further comprises a first end culminating in a tip, a second end having an inner conduit, and one or more through holes between the tip and the second end in fluid communication with the inner conduit forming part of a continuous liquid passageway in fluid communication with the primary chamber, the second end being disposed closer to the primary chamber than the tip.

5. The method of claim 4, wherein
   the outer surface over which the plastic sleeve is heat shrunk is proximate the second end of the spike element.

6. The method of claim 4, wherein
   the one or more through holes of the spike element are 18 gauge in size or larger.

7. The method of claim 4, wherein
   the seal comprises (i) a first end, (ii) a second end, (iii) a seal cap at the first end, (iv) a relaxed state in which the seal forms a liquid tight seal over the through holes of the spike element preventing fluid flow through the valve, and (v) a compressed state in which the tip and the through holes of the spike element extend through the seal cap allowing fluid flow from a source external the intravenous fluid bag, through the through holes, through the inner conduit, and into the primary chamber.

8. The method of claim 7, wherein
   the housing includes a hollow interior that surrounds the tip of the spike element; and
   the inner conduit of the spike element is not in fluid communication with the hollow interior of the housing when the seal is in the relaxed state.

9. The method of claim 7, wherein
   the seal forms a conically shaped cavity in which the tip of the spike element is disposed when the seal is in the relaxed state.

10. The method of claim 7, wherein
    the seal comprises a plurality of ringed wall portions that collapse when the seal moves from the relaxed state to the compressed state.

11. The method of claim 7, wherein
    the seal cap comprises a piercing through which the tip and the through holes of the spike element extend when the seal is in the compressed state; and
    when the seal is in the relaxed state, the piercing is closed and does not permit flow of fluid through the seal cap.

12. The method of claim 7, wherein
    the first end of the seal comprises a flat external surface not covered by the housing.

13. The method of claim 12, wherein
    the housing has a first end that is open forming an opening; and
    the first end of the housing at the opening and the flat external surface of the seal are flush.

14. The method of claim 1, wherein the outer surface is cylindrical.

15. The method of claim 1, wherein the intravenous fluid bag further comprises an antimicrobial coating, which comprises a silane quaternary ammonium ion or salt thereof.

\* \* \* \* \*